United States Patent
Sternick

(10) Patent No.: US 11,306,282 B1
(45) Date of Patent: Apr. 19, 2022

(54) MODULAR MULTIPLE MEDIA TRAY SYSTEM

(71) Applicant: John L. Sternick, Brandon, SD (US)

(72) Inventor: John L. Sternick, Brandon, SD (US)

(*) Notice: Subject to any disclaimer, the term of this patent is extended or adjusted under 35 U.S.C. 154(b) by 25 days.

(21) Appl. No.: 15/473,929

(22) Filed: Mar. 30, 2017

(51) Int. Cl.
| | |
|---|---|
| *C12M 1/00* | (2006.01) |
| *C12M 1/16* | (2006.01) |
| *C12M 1/12* | (2006.01) |
| *C12M 3/00* | (2006.01) |
| *C12M 1/107* | (2006.01) |

(52) U.S. Cl.
CPC ............ *C12M 23/04* (2013.01); *C12M 23/36* (2013.01); *C12M 23/38* (2013.01); *C12M 23/44* (2013.01); *C12M 23/46* (2013.01); *C12M 23/48* (2013.01); *C12M 23/50* (2013.01); *C12M 29/20* (2013.01)

(58) Field of Classification Search
CPC ...... C12M 23/04; C12M 23/36; C12M 23/38; C12M 23/44; C12M 23/46; C12M 23/48; C12M 23/50; C12M 29/20
USPC ........... 435/87.1, 287.7, 288.3, 288.4, 288.7, 435/289.1, 305.3
See application file for complete search history.

(56) References Cited

U.S. PATENT DOCUMENTS

| | | | |
|---|---|---|---|
| 3,532,604 A | | 10/1970 | Bloch |
| 3,540,985 A | * | 11/1970 | Gross ..................... C12M 23/10 435/288.3 |
| 3,728,228 A | * | 4/1973 | Duranty ................ B01L 3/5085 435/288.3 |
| 4,072,577 A | | 2/1978 | Hirshaut |
| 4,591,556 A | * | 5/1986 | Saxholm ................ C12M 29/00 422/502 |
| 4,847,128 A | | 7/1989 | Dorn |

(Continued)

FOREIGN PATENT DOCUMENTS

| | | | |
|---|---|---|---|
| CN | 202626182 U | * 12/2012 | ............ C12M 23/10 |
| EP | 0119984 | 2/1984 | |

(Continued)

OTHER PUBLICATIONS

Courvalin, "English machine translation of patent application FR-2543157-A1". (Year: 1984).*

(Continued)

*Primary Examiner* — Liban M Hassan
(74) *Attorney, Agent, or Firm* — Jeffrey A. Proehl; Woods Fuller Shultz & Smith PC

(57) ABSTRACT

A system may include a base assembly having a top and a bottom restable on a surface, with the base assembly comprising at least one trough having an upper opening into a cavity and a trough holder configured to hold the at least one trough. The system may also include a cover assembly mounted on the base assembly and configured to cover the at least one trough in the holder. The cover assembly may comprise a main cover portion including a cover wall extending over the at least one trough, with at least one aperture extending through the main cover portion and being substantially vertically aligned with the cavity of the at least one trough mounted on the base assembly. The cover assembly may also include a disc pressure portion configured to removably insert into the at least one aperture press against a disc positioned at the aperture of the main cover portion to move the disc toward the cavity of the at least one trough.

13 Claims, 15 Drawing Sheets

(56) References Cited

U.S. PATENT DOCUMENTS

| | | | |
|---|---|---|---|
| 4,868,110 A * | 9/1989 | DesRosier | C12M 23/08 435/34 |
| 5,520,302 A | 5/1996 | Anderson | |
| 5,650,125 A * | 7/1997 | Bosanquet | B01L 3/5021 422/548 |
| 5,661,029 A * | 8/1997 | Self | G02B 21/34 359/398 |
| 6,153,400 A * | 11/2000 | Matsumura | C12Q 1/18 435/283.1 |
| 7,384,778 B2 * | 6/2008 | Chen | B01L 3/50853 435/287.1 |
| 2004/0013576 A1 * | 1/2004 | Gfrorer | B01F 5/10 422/561 |
| 2005/0003525 A1 | 1/2005 | Hsu | |
| 2007/0172944 A1 * | 7/2007 | Li | C12M 23/12 435/297.5 |
| 2009/0310839 A1 * | 12/2009 | Katzenelson | C12Q 1/025 382/128 |
| 2010/0099137 A1 * | 4/2010 | Taintor | C12Q 1/18 435/32 |
| 2011/0003376 A1 | 1/2011 | Gulzow | |
| 2011/0189782 A1 | 8/2011 | Testa | |
| 2013/0095009 A1 | 4/2013 | Huet | |

FOREIGN PATENT DOCUMENTS

| | | | | |
|---|---|---|---|---|
| EP | 0171174 | | 2/1986 | |
| EP | 1035201 | | 9/2000 | |
| FR | 2543157 | A1 * | 9/1984 | C12M 21/16 |
| FR | 2795089 | | 12/2000 | |
| WO | WO-2011135583 | A2 * | 11/2011 | C12M 99/00 |

OTHER PUBLICATIONS

Ni et al., "English machine translation of patent application CN-202626182-U". (Year: 2012).*

\* cited by examiner

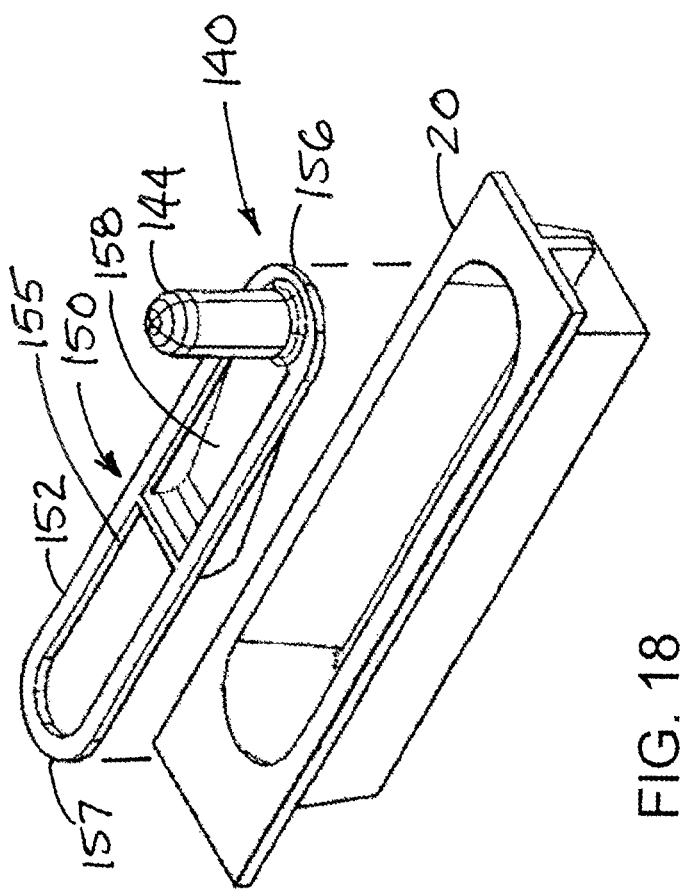
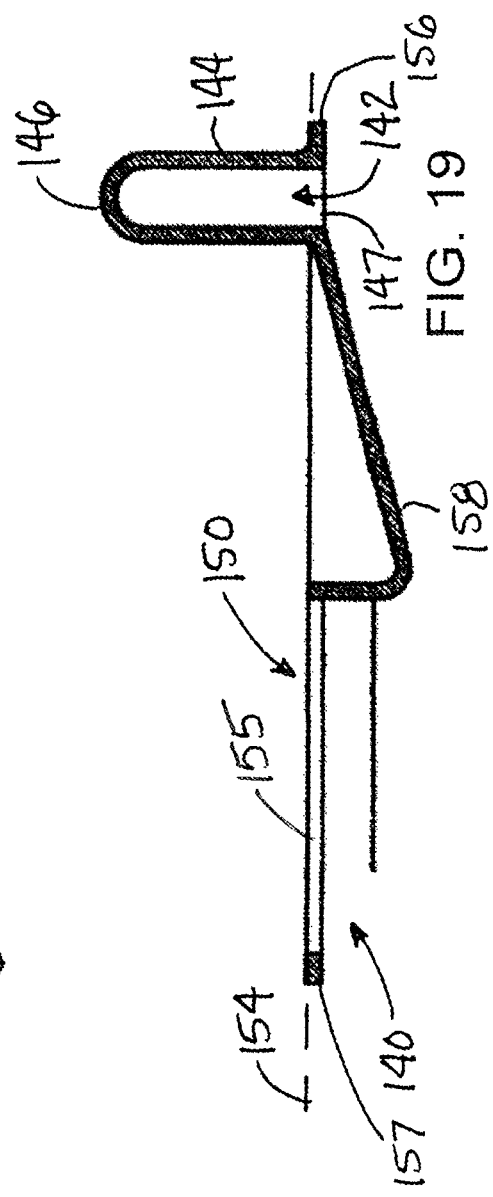
FIG. 18
FIG. 19

MODULAR MULTIPLE MEDIA TRAY SYSTEM

BACKGROUND

Field

The present disclosure relates to laboratory tools and more particularly pertains to a new modular multiple media tray system for facilitating laboratory procedures utilizing organism growth on a medium.

SUMMARY

The present disclosure relates to a system which may comprise a base assembly having a top and a bottom restable on a surface. The base assembly may comprise at least one trough having an upper opening into a cavity and a trough holder configured to hold the at least one trough. The system may also include a cover assembly mounted on the base assembly and configured to cover the at least one trough in the holder. The cover assembly may comprise a main cover portion including a cover wall extending over the at least one trough, with at least one aperture extending through the main cover portion and being substantially vertically aligned with the cavity of the at least one trough mounted on the base assembly. The cover assembly may also include a disc pressure portion configured to removably insert into the at least one aperture press against a disc positioned at the aperture of the main cover portion to move the disc toward the cavity of the at least one trough.

There has thus been outlined, rather broadly, some of the more important elements of the disclosure in order that the detailed description thereof that follows may be better understood, and in order that the present contribution to the art may be better appreciated. There are additional elements of the disclosure that will be described hereinafter and which will form the subject matter of the claims appended hereto.

In this respect, before explaining at least one embodiment or implementation in greater detail, it is to be understood that the scope of the disclosure is not limited in its application to the details of construction and to the arrangements of the components, or the particulars of the steps, set forth in the following description or illustrated in the drawings. The disclosure is capable of other embodiments and implementations and is thus capable of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

The advantages of the various embodiments of the present disclosure, along with the various features of novelty that characterize the disclosure, are disclosed in the following descriptive matter and accompanying drawings.

BRIEF DESCRIPTION OF THE DRAWINGS

The disclosure will be better understood and when consideration is given to the drawings and the detailed description which follows. Such description makes reference to the annexed drawings wherein:

FIG. 18 is a schematic perspective view of an illustrative embodiment of a gas capture structure shown in exploded in exploded relationship with a trough.

FIG. 19 is a schematic side sectional view of the gas capture structure shown in FIG. 18.

DETAILED DESCRIPTION

Figure 1:
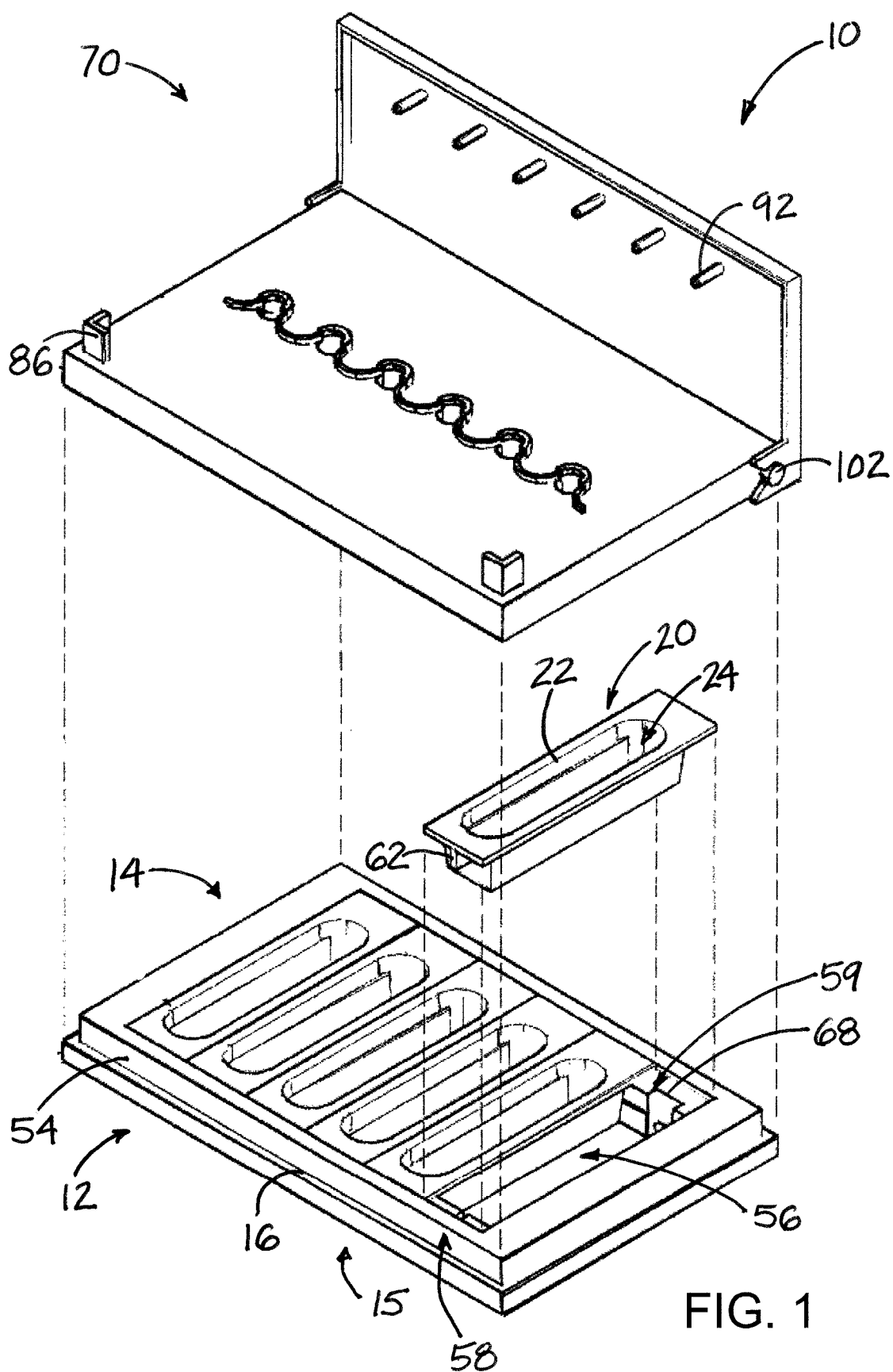
FIG. 1 is a schematic exploded perspective view of elements of a new modular multiple media tray system according to the present disclosure.

With reference now to the drawings, and in particular to FIGS. 1 through 23 thereof, a new modular multiple media tray system embodying the principles and concepts of the disclosed subject matter will be described.

Various laboratory procedures are conducted in containers or plates sometimes referred to as "Petri dishes" which are generally shallow and round, and typically contain a medium on (or in) which various substances or organisms are placed for a period of time to observe activity (or inactivity). For example, one laboratory process involves determining the susceptibility of an organism to various antibiotics at various strengths. The Kirby-Bauer method places an antibiotic-impregnated disc on the surface of an agar material in a plate on which a bacteria has been applied. A zone of inhibition may be formed about the disc which corresponds to the effectiveness against the bacterium of the antibiotic at the specific strength in the impregnated disc. The relative size of the inhibition zones of the various antibiotics and strengths indicates the relative effectiveness of the combination of antibiotic and strength on the subject bacterium. Other methods, such as the ETEST method, utilize similar zones of inhibition about a strip impregnated with an antibiotic at concentrations or strengths that vary along the length of the strip.

Typically the process is carried out on a common circular plate with agar material, and the applicant has recognized that this traditional approach can leave a significant portion of the agar material essentially unused since the discs must be placed on the agar surface at sufficient spacing to accommodate the largest likely zone of inhibition, as the actual size of the zone of inhibition is unpredictable and placing the discs too close together may result in overlapping zones which can complicate or even render impossible an interpretation of the relative effectiveness of the antibiotic/ strength combinations corresponding to the overlapping inhibition zones.

The applicant has recognized that practice using conventional plates either sacrifices accuracy in order to minimize usage of the plates and the agar material, or creates waste in order to provide the greatest accuracy. The applicant has developed a system which more effectively matches the use of laboratory materials to the number of tests that need to be conducted and for each test conducted, can minimize the amount of agar material used to conduct the test. Further, the system may facilitate the placement of the disks on the surface of the agar material, and may also facilitate testing under anaerobic conditions as well as aerobic conditions. Also, the system may include elements that facilitate the measurement of the magnitude of the zone of inhibition for each sample. Still further, the system may include components that facilitate the capture of any gases produced by an organism or reaction.

In one aspect, the disclosure relates to a system 10 which is highly suitable for performing laboratory procedures, such as the procedures discussed above but also for other procedures such as microbial identification.

Figure 2:
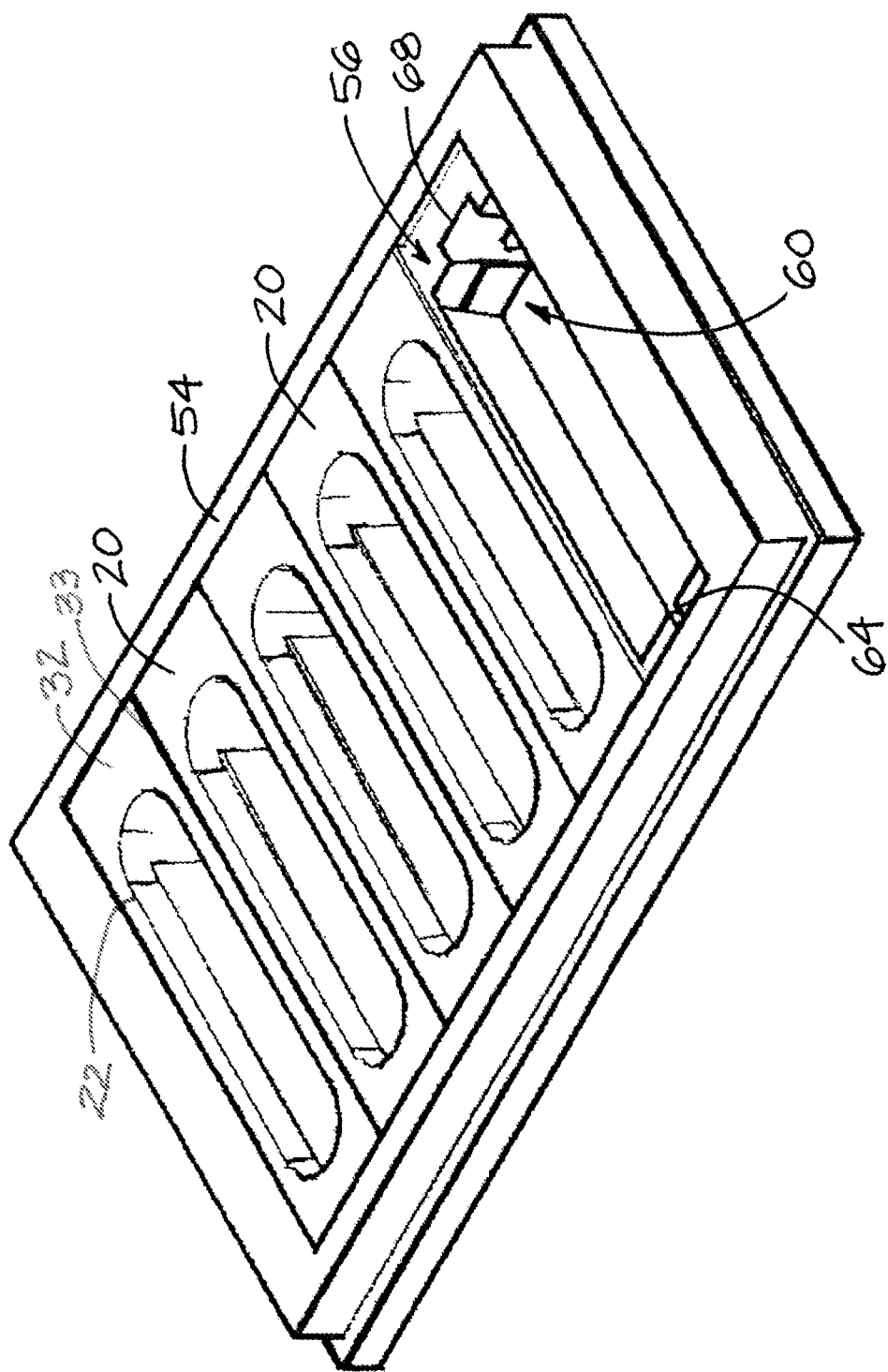
FIG. 2 is a schematic perspective view of the base assembly, according to an illustrative embodiment.
Figure 3:
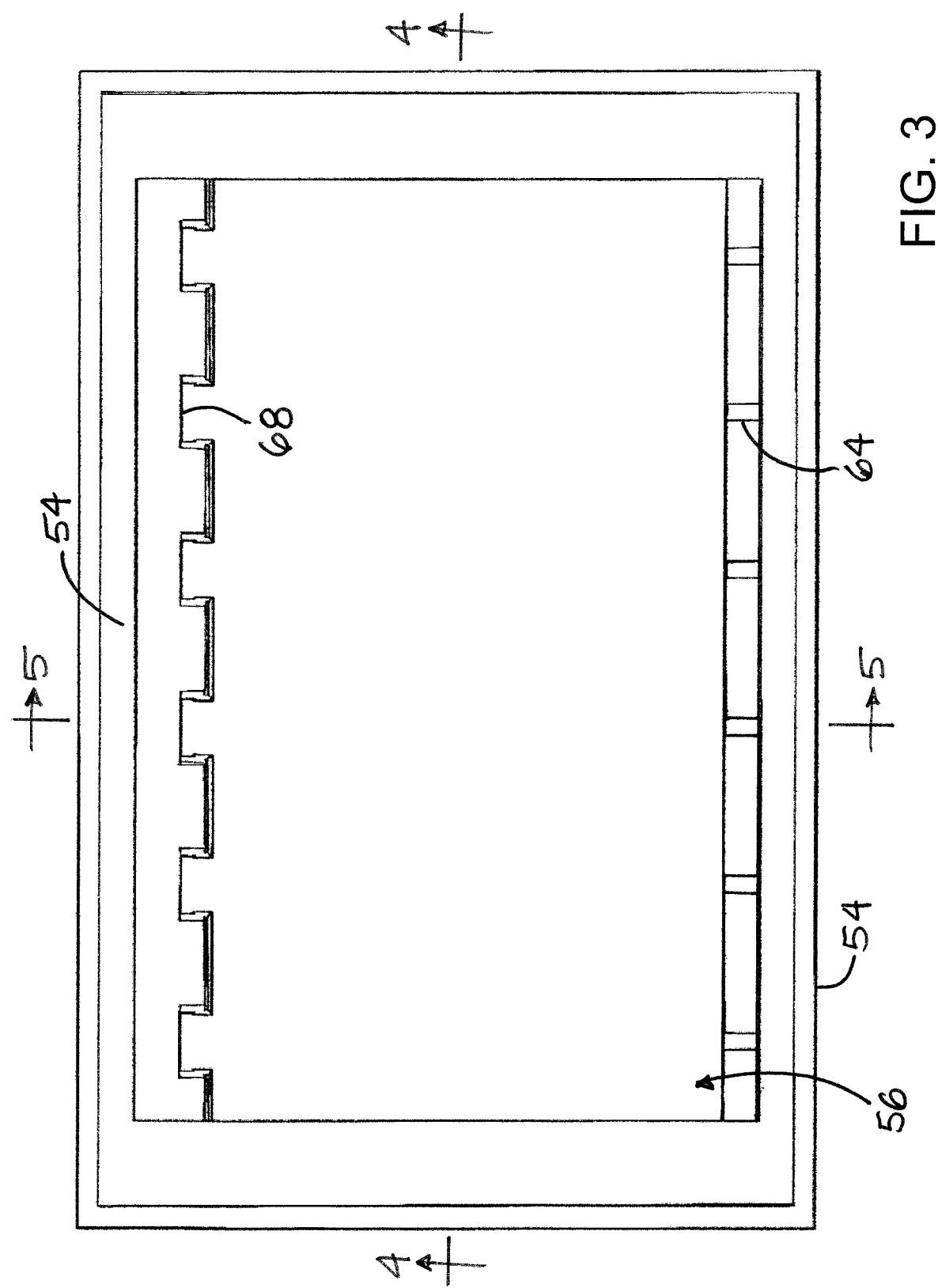
FIG. 3 is a schematic top view of the base portion, according to an illustrative embodiment.
Figure 4:
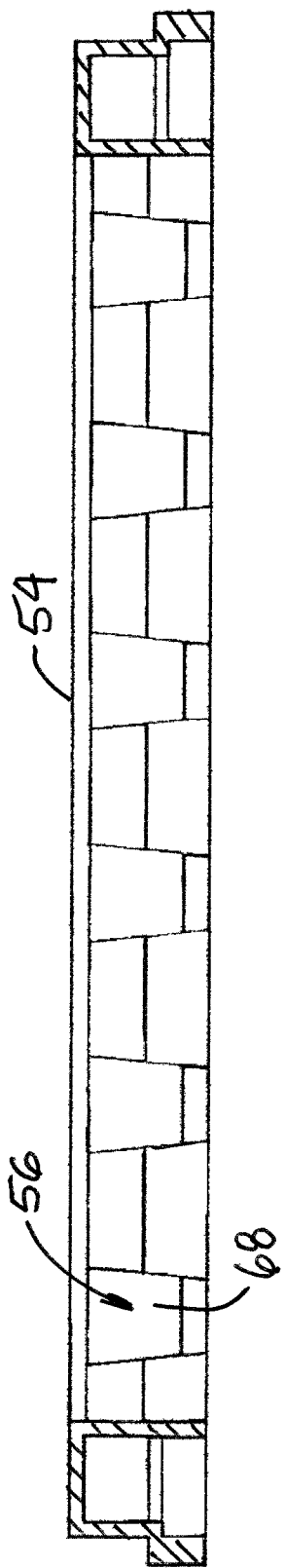
FIG. 4 is a schematic side sectional view of the base portion, according to an illustrative embodiment, taken along line 4-4 in FIG. 3.
Figure 5:
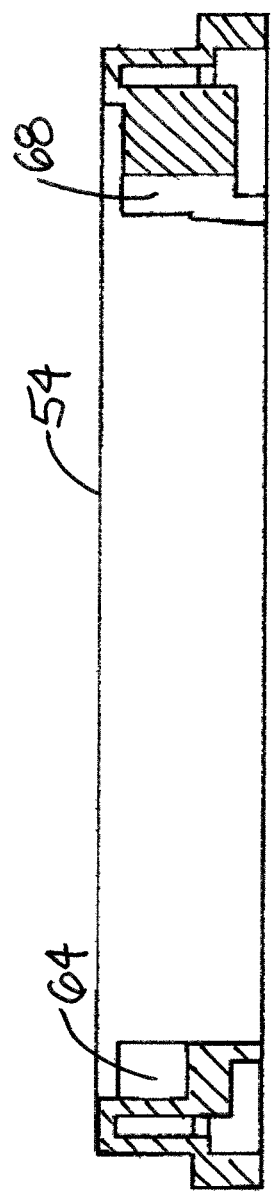
FIG. 5 is a schematic end sectional view of the base portion, according to an illustrative embodiment, taken along line 5-5 in FIG. 3.
Figure 6:
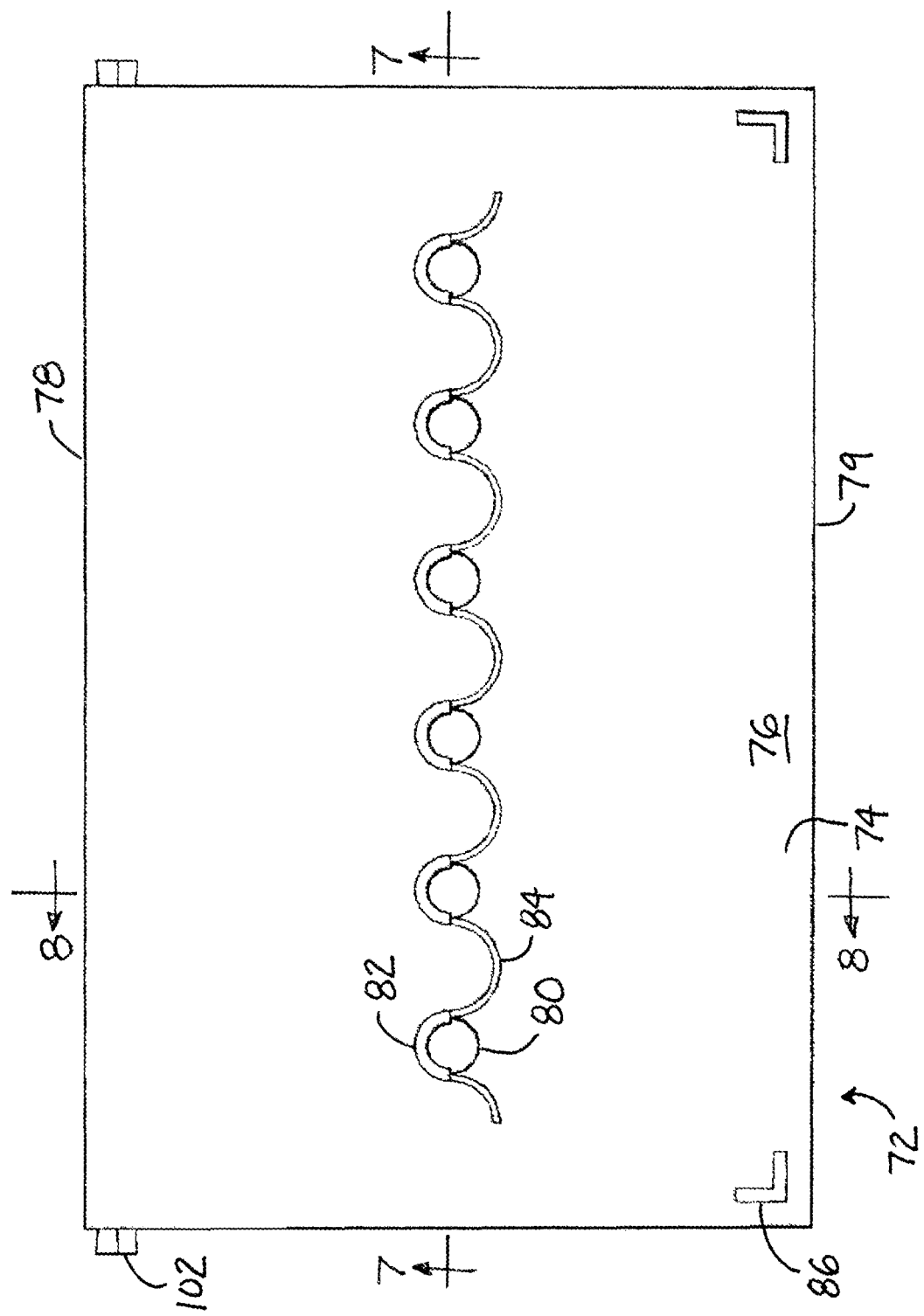
FIG. 6 is a schematic top view of the main cover portion, according to an illustrative embodiment.
Figure 7:
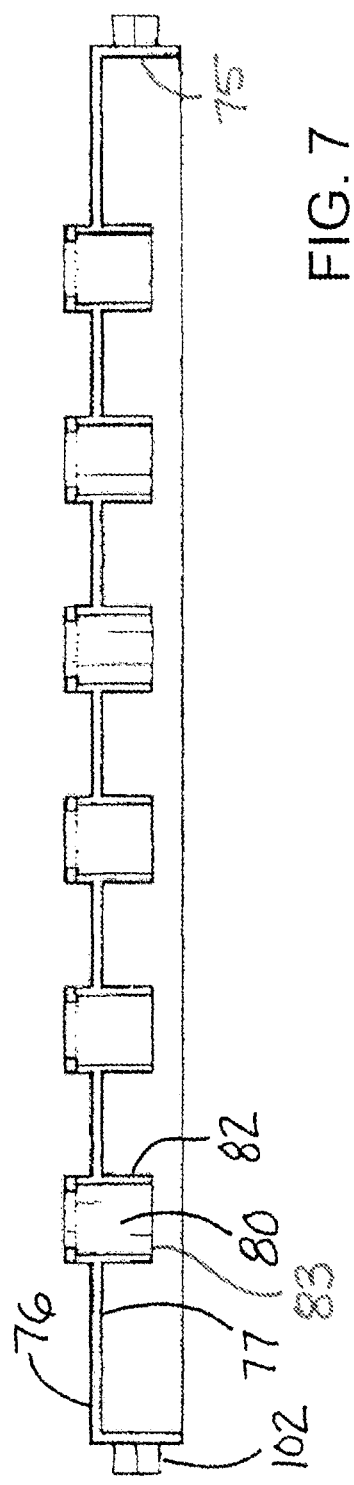
FIG. 7 is a schematic side sectional view of the main cover portion, according to an illustrative embodiment, taken along line 7-7 in FIG. 6.
Figure 8:
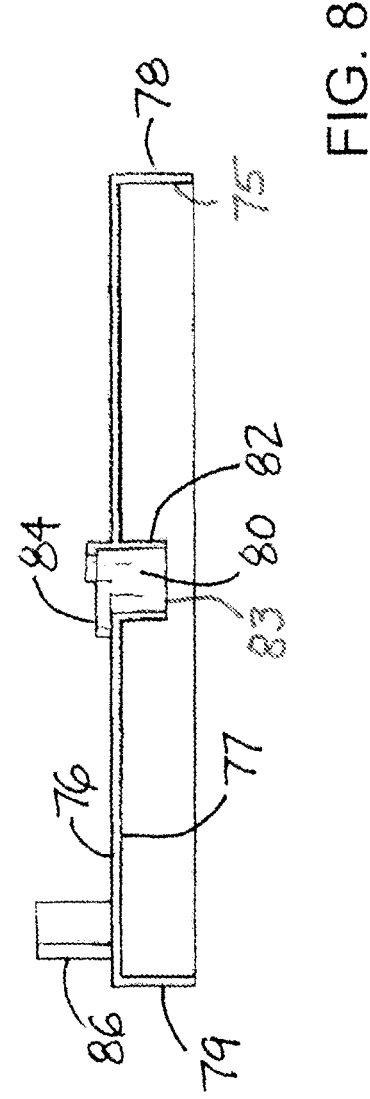
FIG. 8 is a schematic end sectional view of the main cover portion, according to an illustrative embodiment, taken along line 8-8 in FIG. 6.
Figure 9:
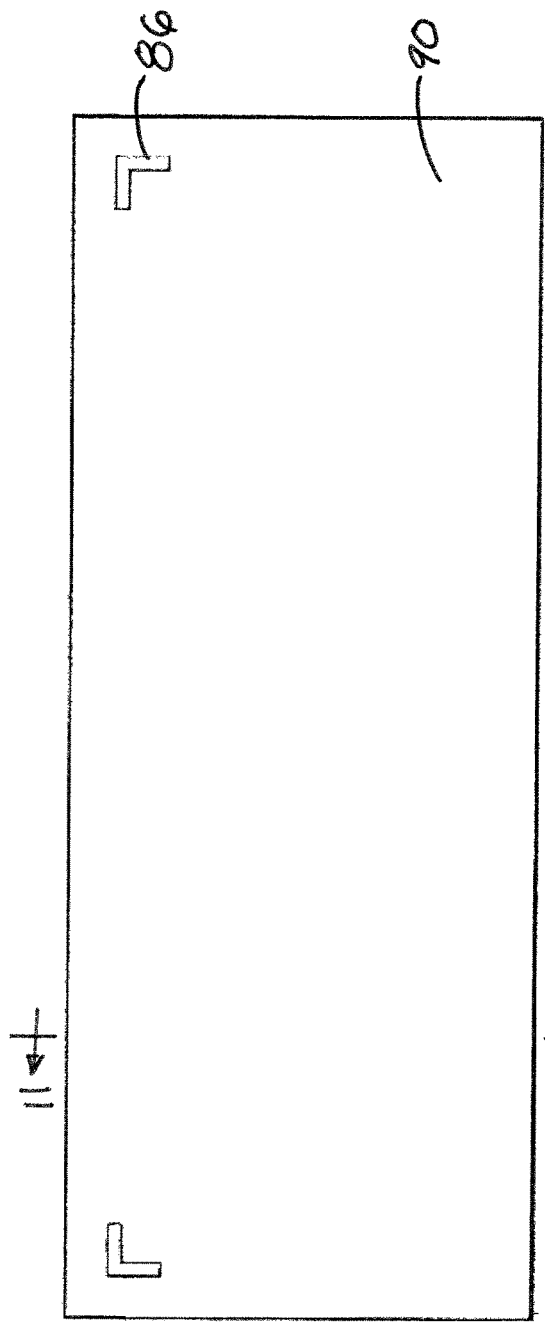
FIG. 9 is a schematic top view of the disc pressure portion, according to an illustrative embodiment.
Figure 10:
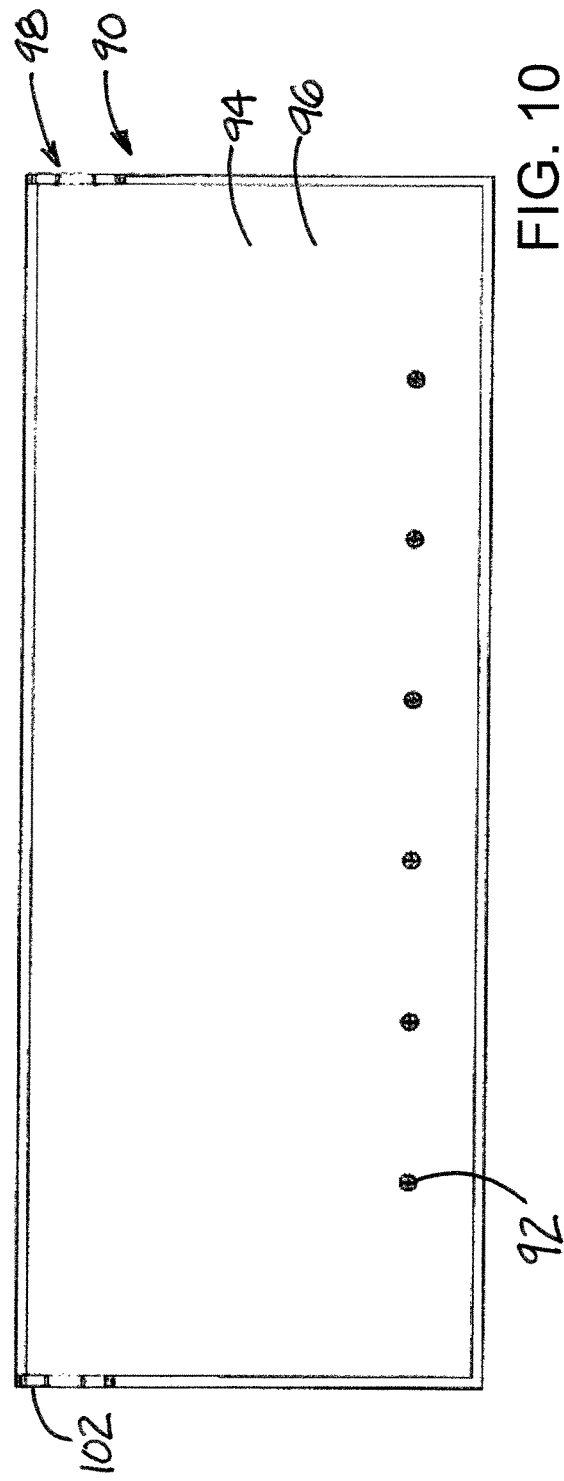
FIG. 10 is a schematic bottom view of the disc pressure portion, according to an illustrative embodiment.
Figure 11:
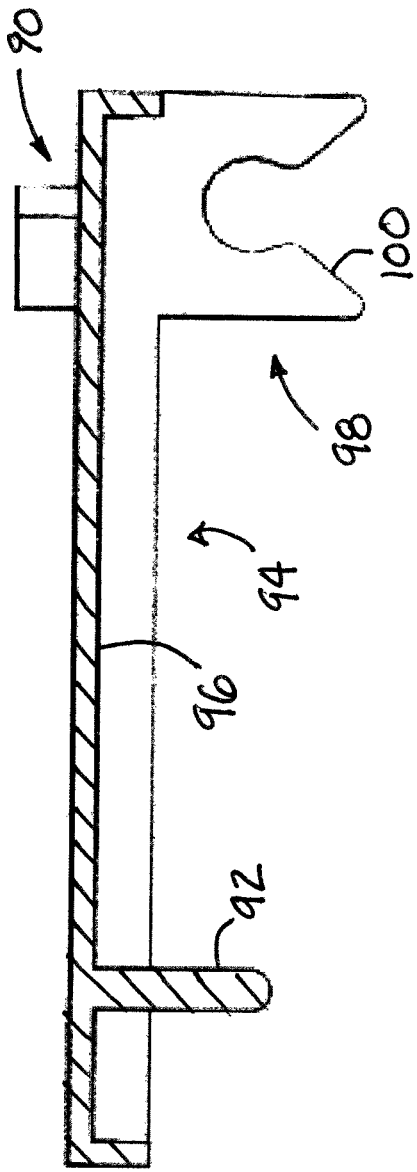
FIG. 11 is a schematic side sectional view of the disc pressure portion, according to an illustrative embodiment, taken along line 11-11 in FIG. 9.
Figure 12:
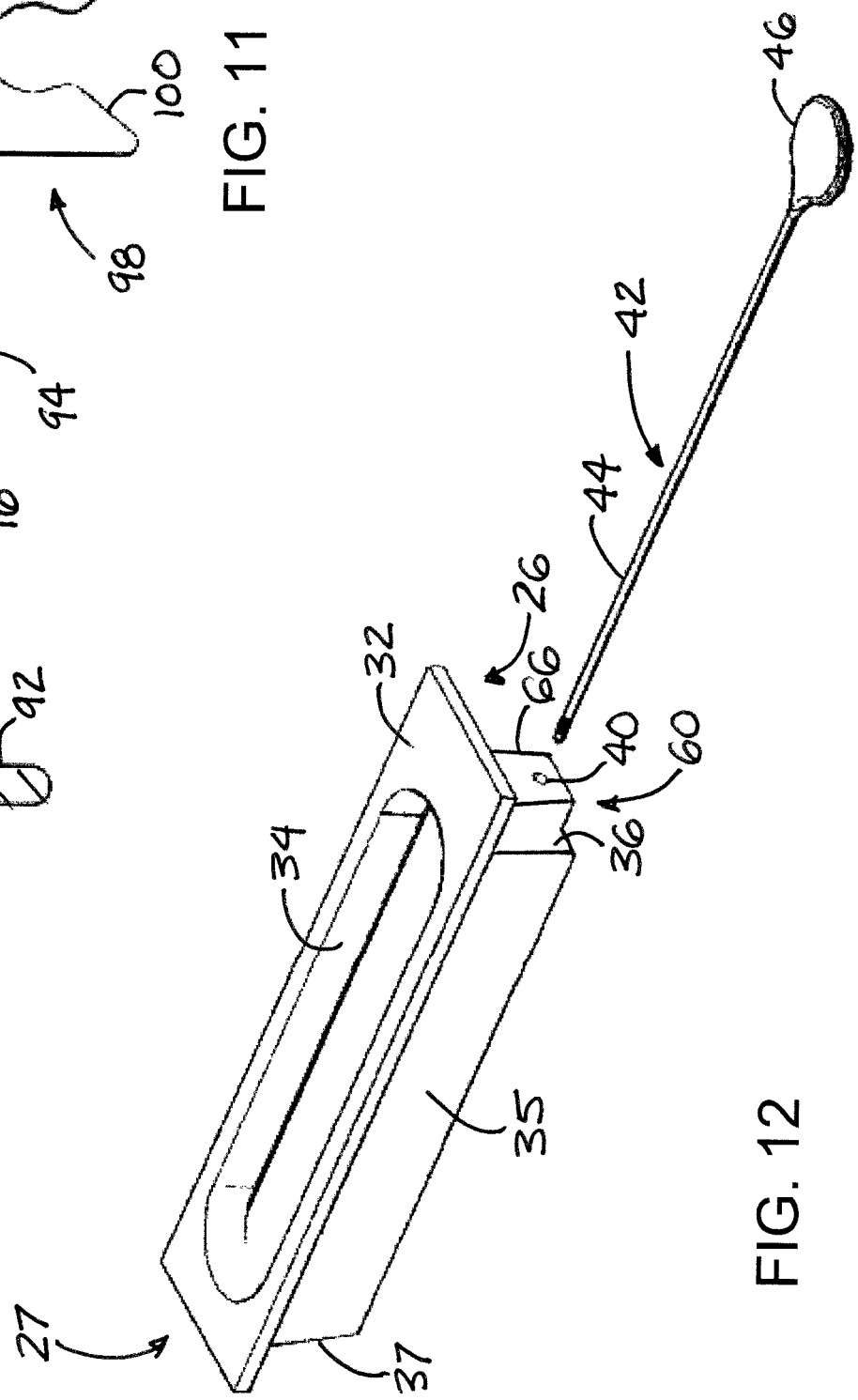
FIG. 12 is a schematic perspective view of a trough and an insertion needle, according to an illustrative embodiment.
Figure 13:
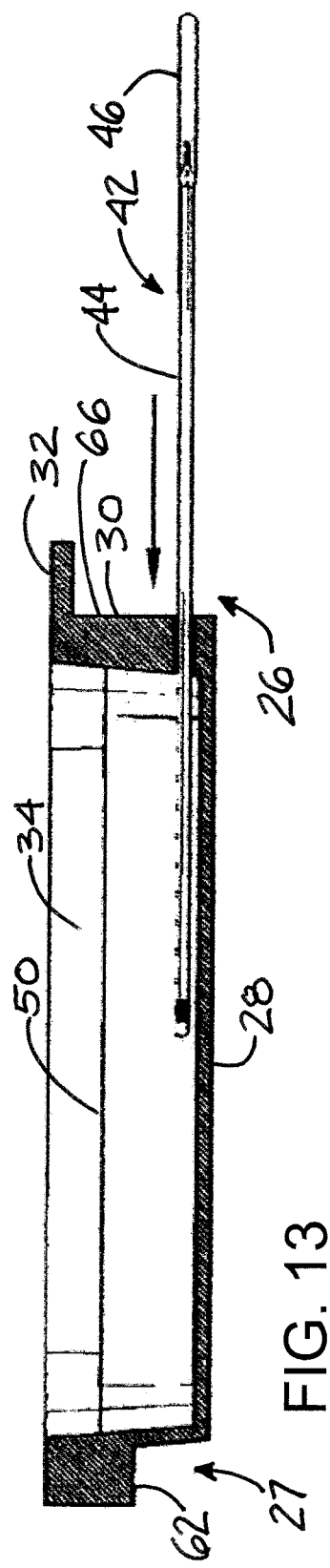
FIG. 13 is a schematic side sectional view of the trough with an insertion needle partially inserted through the needle hole, according to an illustrative embodiment.
Figure 15:
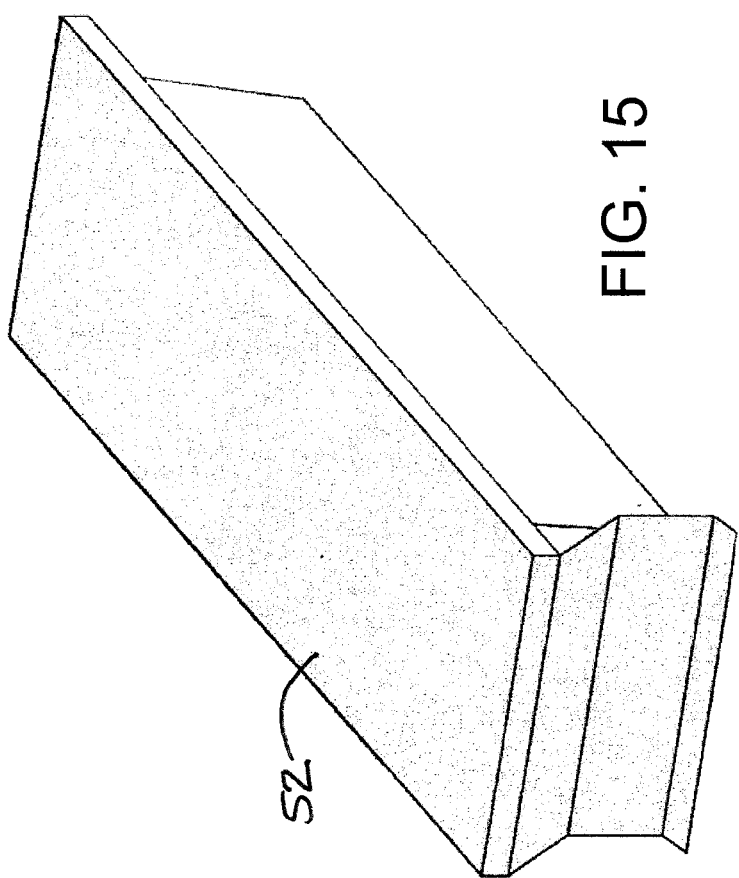
FIG. 15 is a schematic perspective view of a trough with a covering strip, according to an illustrative embodiment.
Figure 14:
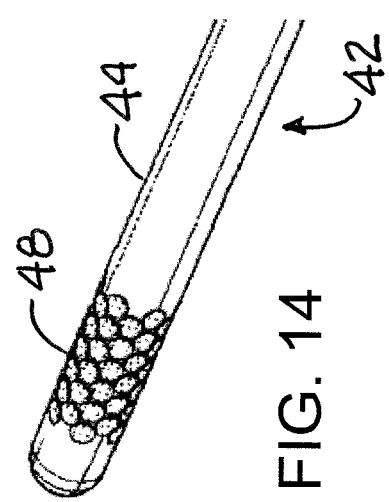
FIG. 14 is a schematic perspective view of a tip portion of the insertion needle, according to an illustrative embodiment.
Figure 16:
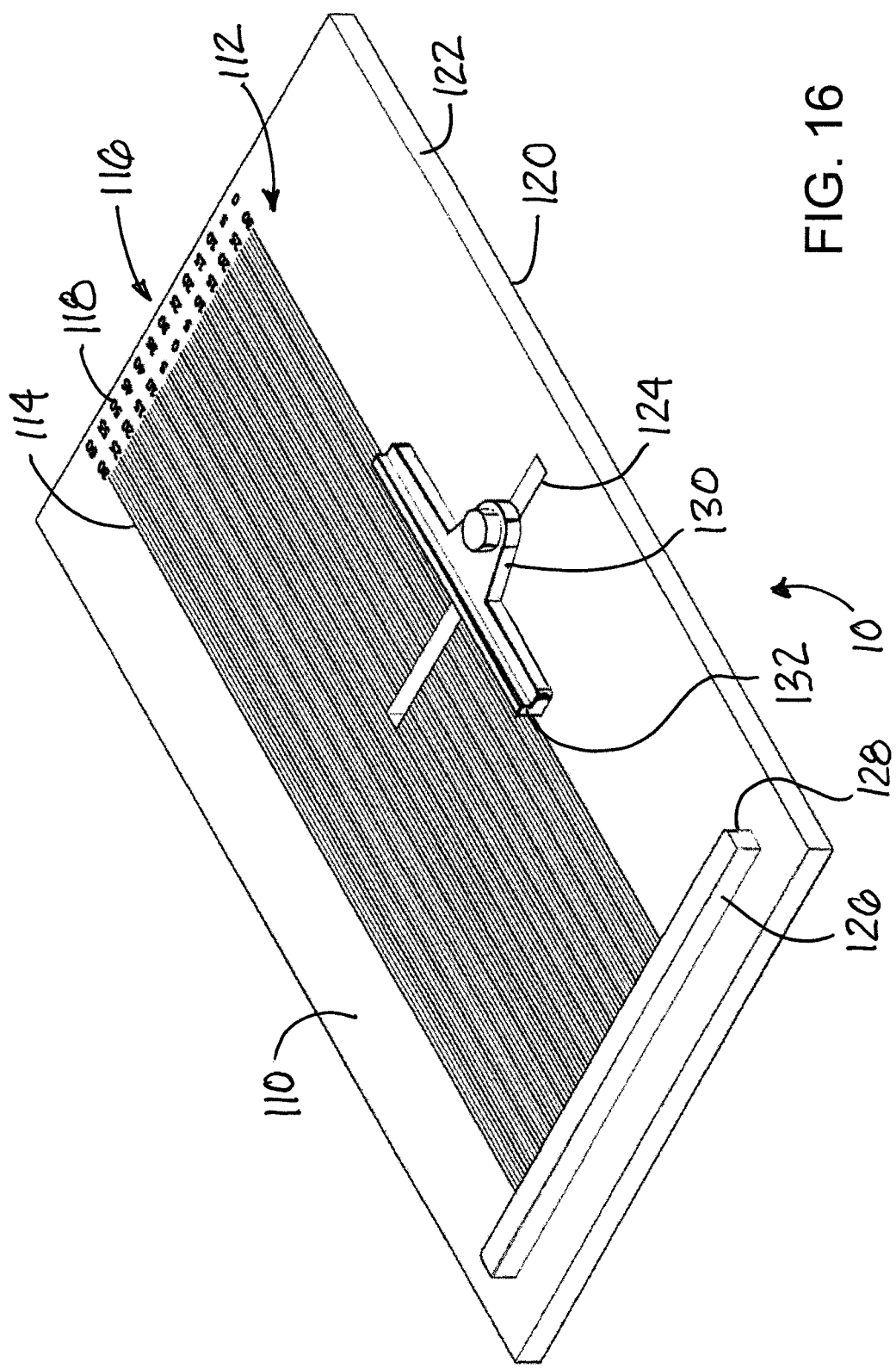
FIG. 16 is a perspective view of a measuring support of the system with a measuring surface, according to an illustrative embodiment.
Figure 17:
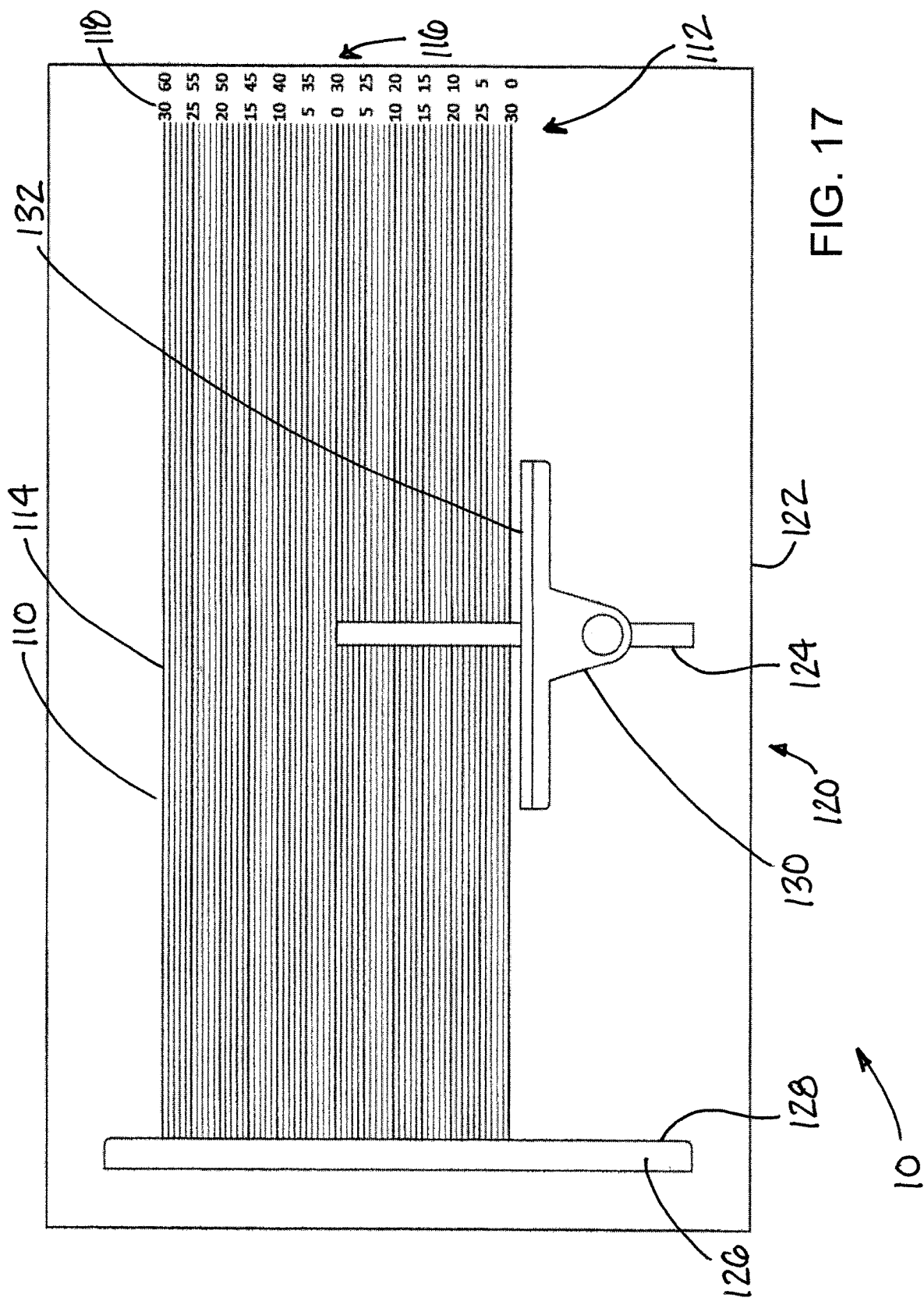
FIG. 17 is a schematic top view of the measuring support with measuring surface, according to an illustrative embodiment.

The system 10 may include a base assembly 12 having a top 14 and a bottom 15 which may be restable on a surface. The base assembly 12 may have a perimeter shoulder 16 which generally extends about the perimeter of the assembly 12. The base assembly may include at least one trough 20 which has an upper opening 22 which opens into a cavity 24 that is generally closed at the bottom in order to hold a material. In some of the most advantageous embodiments, the upper opening 22 and the cavity 24 are elongated along a longitudinal axis of the trough 20 and the upper opening and cavity have an elongated oval shape. The trough has opposite ends 26, 27. Illustratively, the trough 20 may comprise a base wall 28, a perimeter wall 30 which extends upwardly from the base wall, and an upper lip wall 32 which defines the upper opening and extends outwardly from at least portions of the perimeter wall to a perimeter edge 33, and the perimeter edge may be positioned adjacent to the perimeter edge of another trough positioned in an adjacent bay of a trough holder (such as is shown in FIGS. 1 and 2). The upper lip wall 32 may be oriented substantially parallel to the base wall 28, and may extend to the ends 26, 27 of the trough. The distance between the base wall 28 and the upper lip wall 32 defines a depth of the trough, and may vary to provide greater or lesser capacities for the cavity of the trough. The perimeter wall 30 may have a pair of side sections 34, 35 positioned in opposition to each other on either side of the cavity, and a pair of end sections 36, 37 which are also positioned in opposition to each other. In some embodiments of the base assembly, a plurality of the troughs 20 may be utilized, and each of the troughs may be substantially identical to each other so as to be interchangeable with each other.

A trough 20 may have a needle hole 40 which extends through the perimeter wall 30, and may extend through one of the end sections 36 of the perimeter wall, in an orientation which may be substantially parallel to the longitudinal axis of the cavity 24 of the trough and may be substantially parallel to an upper surface of the base wall 28 of the trough. An insertion needle 42 may be configured to be insertable into the cavity of the trough through the needle hole 40 at a level below the upper opening 22 and without passing through the upper opening of the trough to facilitate anaerobic insertion and testing of a substance in the agar material. The insertion needle 42 may have an insertion portion 44 and a gripping portion 46 which is positioned at an end of the insertion portion. A section of the insertion portion 44 may have a roughened surface 48 for carrying a substance in the voids of the roughened surface when inserted through the needle hole.

In some embodiments, an agar material 50 may be positioned in the cavity 24 of the trough to facilitate growth of substances positioned in the cavity of the trough. Optionally, the agar material may be prepackaged in the trough for convenient laboratory use. A covering strip 52 may be mounted on the trough 20 to cover the upper opening 22 of the trough, which may be highly useful for maintaining the sterility of the cavity as well as holding an agar material 50 pre-inserted into the cavity of the trough for use in laboratory processes. The covering strip 52 may be removably adhered to the upper lip wall 32 of the trough, and in some configurations the covering strip may extend beyond one end of the upper lip wall to extend over the needle hole 40 in the trough to thereby close the needle full against contamination and/or leakage.

The base assembly 12 of the system 10 may also include a trough holder 54 for holding at least one of the troughs 20, and in some embodiments may be configured to hold a plurality of the troughs in an array such as in side-by-side relationships. The trough holder 54 may be configured to removably receive multiple troughs such that the troughs may be installed and removed from the holder as needed for the various laboratory operations. The trough holder 54 may define at least one bay 56 which is configured to receive one of the troughs 20, and may be configured to define a plurality of the bays with each bay being configured to removably receive one of the troughs. Each of the bays may have opposite ends 58, 59.

A securing structure 60 may be configured to removably secure a trough in a bay 56. The securing structure may engage the trough in one of the bays with a snap fit to secure the trough in the bay. The securing structure 60 may be located on at least one of the bay ends 58, 59 and at least one of the trough ends 26, 27. In some embodiments, a first securing structure may comprise a blade 62 located on one end of the trough and a slot 64 located on a corresponding end of the bay. A second securing structure may comprise a plug 66 which is located on one end of the trough and a recess 68 which is formed on a corresponding end of the bay. The recess 68 may taper narrower toward the bottom 15 of the base assembly 12. Other suitable securing structures may also be utilized as well.

The system may also include a cover assembly 70 which is mounted on the base assembly 12, and in some embodiments may be removably mounted on the base assembly. The cover assembly 70 may include a main cover portion 72 which may be configured to fit over at least a portion of the base assembly 12 to cover the upper openings of the troughs 20 mounted on the trough holder 54. The main cover portion 72 may include a cover wall 74 for extending over the trough or troughs when the main cover portion is rested on the base assembly. In some embodiments, a periphery of the cover wall 74 of the main cover portion may have a peripheral wall 75 (see FIGS. 7 and 8) which extends away from the cover wall 74 to rest upon the perimeter shoulder 16 of the base assembly. The cover wall 74 may have an upper surface 76 and a lower surface 77 facing the troughs. The cover wall 74 may have opposite sides 78, 79. At least one aperture 80 may be formed on the main cover portion, and may be positioned in a central location between the opposite sides 78, 79 of the cover wall 74 (see, e.g., FIGS. 6 and 8 of the drawings) so that the aperture is positioned centrally over the elongated upper opening of the trough. The aperture 80 may extend through the cover wall 74 from the upper surface 76 to the lower surface 77 of the cover wall. The aperture 80 may be alignable with the cavity of one of the troughs on the trough holder of the base assembly when the cover portion 72 is installed on the base assembly, and multiple apertures may be utilized with each aperture being aligned with the cavity of one of the troughs. Advantageously, each aperture 80 may be positioned above a location on the upper opening 22 which is substantially centered between the ends of the cavity.

In some embodiments, one or more of the apertures 80 may be formed by a tubular structure 82. A portion of the tubular structure 82 may extend above the plane of the upper surface 76 of the cover wall and a section of the tubular structure may also extend below the plane of the lower surface 77. In some embodiments, a section of the portion of the tubular structure extending above the upper surface 76 may be absent, such as approximately one half of the tubular structure, so that the remaining section of the tubular structure portion may help to guide a disc to the aperture 80 when the disc is moved along the upper surface 76 of the cover wall. The portion of the tubular structure 82 may extend below the lower surface 77 of the cover wall 74 to a lowermost end 83 (see, e.g., FIGS. 7 and 8 of the drawings) opposite of the cover wall portion. The sections of the peripheral wall 75 of the main cover portion located at the opposite sides 78, 79 of the cover may extend further from the lower surface 71 than the lowermost end 83 of the tubular structure 82 (see, e.g., FIGS. 7 and 8). The portion of the tubular structure 78 below the cover wall 74 may help to guide the disc into the cavity 24 of the respective trough 20 above which the aperture is aligned. An arcuate ridge 84 may be located on the upper surface 76 of the cover wall and extend between the tubular structures of adjacent apertures 80 to form a substantially serpentine shape with the remaining portions of the tubular structures located above the upper surface to further facilitate the guidance of a disc into each of the apertures 80.

Optionally, at least one positioning nub 86 may be located on the upper surface 76 of the cover wall for interlocking with the bottom 15 of the base portion of another system 20 to facilitate stacking of the systems on top of each other and also minimizing opportunity for the systems to slide off of each other when stacked.

The cover assembly 70 may also include a disc pressure portion 90 which is configured to push or press against a disc located in the aperture 80 of the main cover portion. This pressure portion 90 may be positioned over the upper surface 76 of the cover wall when the portion 90 is mounted on the main cover portion 72. The pressure portion 90 may include at least one pressure post 92, and the pressure portion 90 may be movable with respect to the main cover portion in order to cause at least a section of the pressure post 92 to move into (and out of) the aperture 80 in the cover wall. In some embodiments, the disc pressure portion 90 is pivotally mounted on the main cover portion so as to move the pressure post 90 in a substantially arcuate path into and out of the aperture 80. A plurality of the pressure posts 92 may be utilized such that each of the apertures 80 in the main cover portion has an associated pressure post movable into and out of the aperture by movement of the disc pressure portion 90.

In some embodiments, the disc pressure portion 90 may include a support 94 which is pivotally mounted on the main cover portion 72 so as to rotate about an axis. The support 94 may include a support wall 96 and a mounting structure 98 which is configured to mount the support wall on the main cover portion. The mounting structure 98 may include at least one clip 100 which is located on the support wall. Illustratively, a pair of the clips 100 may be mounted on spaced locations on the support wall. The mounting structure may further include a pivot post 102 which extends from the main cover portion and is engaged by one of the clips 100 such that the clip is able to rotate on the pivot post about the axis. A pair of the pivot posts 102 may be mounted on the main cover portion and may extend in substantially opposite directions to be engaged by the pair of clips 100.

In use, one or more troughs may be positioned in the trough holder with an agar medium positioned in the trough. The bacterium may be spread across the exposed surface of the agar medium, in an aerobic test, or may be inserted into the agar medium by applying the bacterium to the roughened surface of the insertion needle and inserting the needle through the needle hole and into the solid medium for an anaerobic test. The cover assembly may be closed over the trough or troughs with the disc pressure posts being withdrawn from the apertures, such as by pivoting the disc pressure portion upwardly with respect to the main cover portion. An antibiotic-impregnated disc may be moved into one or more of the apertures corresponding to one or more of the troughs, with the discs varying in some characteristic such as by antibiotic by concentration of antibiotic. The pressure posts may be moved into the apertures by pivoting the disc pressure portion downwardly to move the posts into the apertures, such that the posts contact the discs located in the apertures and move the discs downwardly into contact with the upper surface of the anchor material. After a suitable period of time, a measurement of the zone of inhibition may be made for each of the troughs and the corresponding discs, in order to determine the relative effectiveness of the associated antibiotic and concentration against the bacteria.

Optionally, the system 10 may include a measuring surface 110 which may facilitate the measuring of the relative size of the inhibition zone of a sample in one trough as compared to the sample in another trough. Forming the trough of the base assembly out of a transparent or substantially transparent material may allow the user to view the contents of the troughs, and the inhibition zone created in the troughs, against a background that may include markings that facilitate comparison of the sizes of the inhibition zones in the troughs. The measuring surface 110 may include a plurality of graduated markings 112 on the measurement surface. The measurement surface 110 may be planar or flat, and may be configured to have the base assembly rested thereon such that the user may peer downwardly on the troughs and view the markings on the measurement surface through the transparent troughs and the agar with the inhibition zones. The graduated markings 112 may include a plurality of lines 114 which extend across a portion of the measuring surface 110. The lines may be oriented substantially parallel to each other and may be substantially equally spaced. The distances between the adjacent lines may or may not correspond to a system of measurement of distances, such as, for example, millimeters or tenths of an inch, etc. The plurality of graduated markings may include a line positioned at a center 116 of the plurality of lines. The graduated markings may also include a plurality of measurement indicia 118 which may each be associated with at least some of the lines of the graduated markings. The measurement indicia may comprise integer numbers that begin count at one side of the plurality of lines and continue to the other side, and/or may count outwardly from the line at the center outwardly in both directions from the center line.

The measuring surface 110 may be provided on a measuring support 120 which has an upper surface a portion of which forms the measuring surface 110. The measuring support may have a perimeter 122, and the perimeter may have a size that is greater than the size of the base assembly 12 in order to permit movement of the base assembly on the upper surface without moving beyond the perimeter 122. The perimeter 122 may be substantially rectangular in shape. A guide groove 124 may be formed in the upper surface of the measuring support and may thus extend through the measuring surface 110. The guide groove 124 may be elongated in a direction which is substantially perpendicular to the direction of the lines 114 of the gradated markings. A stop 126 may be provided on the support 120, and may have a stop surface 128 which extends upwardly from the upper surface of the measuring support. The stop surface 128 may be oriented substantially perpendicular to the measuring surface 110. The stop surface 128 may extend substantially perpendicular to the lines 114 of the gradated markings.

A slider 130 may be abuttable against the base assembly 12 and may be slidable across the upper surface of the measuring support 120 in order to facilitate movement of the base assembly 12, as well as the troughs 20 mounted thereon, with respect to the measuring surface and the gradated markings 112 thereon. The slider 130 may have a slider surface 132 which extends generally upwardly from the measuring surface, and may also extend substantially parallel to the lines 114 of the gradated markings. The slider 130 may engage the guide groove 124 to facilitate movement of the slider, and the slider surface 132, across the measuring surface in a direction that is substantially perpendicular to the lines 114. The slider may thus be used to maintain a side of the base assembly in a parallel orientation with respect to the lines of the gradated markings, while allowing movement of the base assembly and troughs across the measurement surface.

Illustratively, an end of the base assembly 12 with one or more troughs 20 may be abutted against the stop surface, and/or a side of the base assembly may be rested against the slider surface 132, and the base assembly may be slid across the upper surface of the measuring support using the slider 130 with the purpose of aligning the disc with, for example, the line positioned at the center 116 of the plurality of lines so that the furthest extents of the zones for each of the discs may be compared.

In some embodiments, the system 10 may include a gas capture structure 140 which defines a gas capture chamber 142 for capturing gases released by substances contained in the trough 20. The gas capture structure 140 may be configured to (initially) purge gases (such as air) from the gas capture chamber prior to use in order to facilitate accurate capture of gases generated which are sought to be analyzed. The gas capture structure 140 may be removably mountable on the trough 20, and may extend across the upper opening 22 of the trough to facilitate interception and capture of the gases produced. Illustratively, the gas capture structure may extend between the side sections 34, 35 of the perimeter wall 30. The gas capture structure 140 may comprise a gas capture tube 144 which defines the gas capture chamber 142 therein. The gas capture tube may have an upper end 146 for being oriented upwardly during use and a lower end 147 for being oriented downwardly when in use. The gas capture tube 144 may be open on the lower end and closed on the upper end.

One illustrative embodiment of the gas capture structure is shown in FIGS. 18 and 19 and has the gas capture tube mounted on a mounting frame 150 for attachment to the trough. The mounting frame may have a perimeter edge 152 for positioning adjacent to the perimeter wall of the trough adjacent to the upper opening 22. The perimeter may define a perimeter plane 154. The gas capture tube may be located toward a first end 156 of the mounting frame. The mounting frame may define a gas release aperture 155 which may be located at a second end 157 of the mounting frame. The mounting frame may have an air block element 158 which is positioned between the gas capture tube 144 and the gas release aperture 155. The air block element 158 may extend from the perimeter plane to a degree air a greater degree toward the gas release aperture and to a lesser degree toward the gas capture tube. In use, the gas capture structure may be mounted on the trough and the second end of the assembly may be raised until all gas has left the chamber 142, and the assembly may be returned to the normal or level orientation in which gases produced in the trough interior below the gas capture chamber 142 may be directed to and captured by the gas capture tube.

Figure 21:
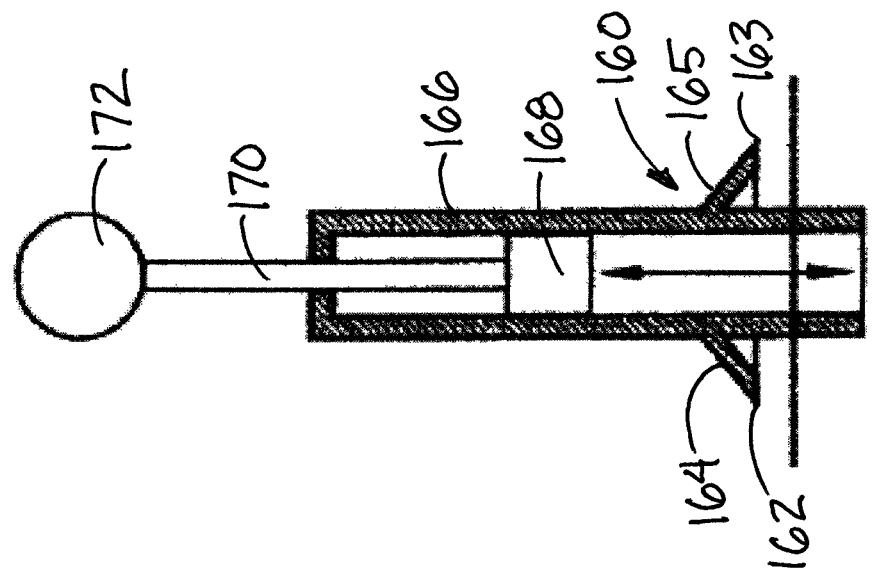
FIG. 21 is a schematic side sectional view of the gas capture structure shown in FIG. 20.
Figure 20:
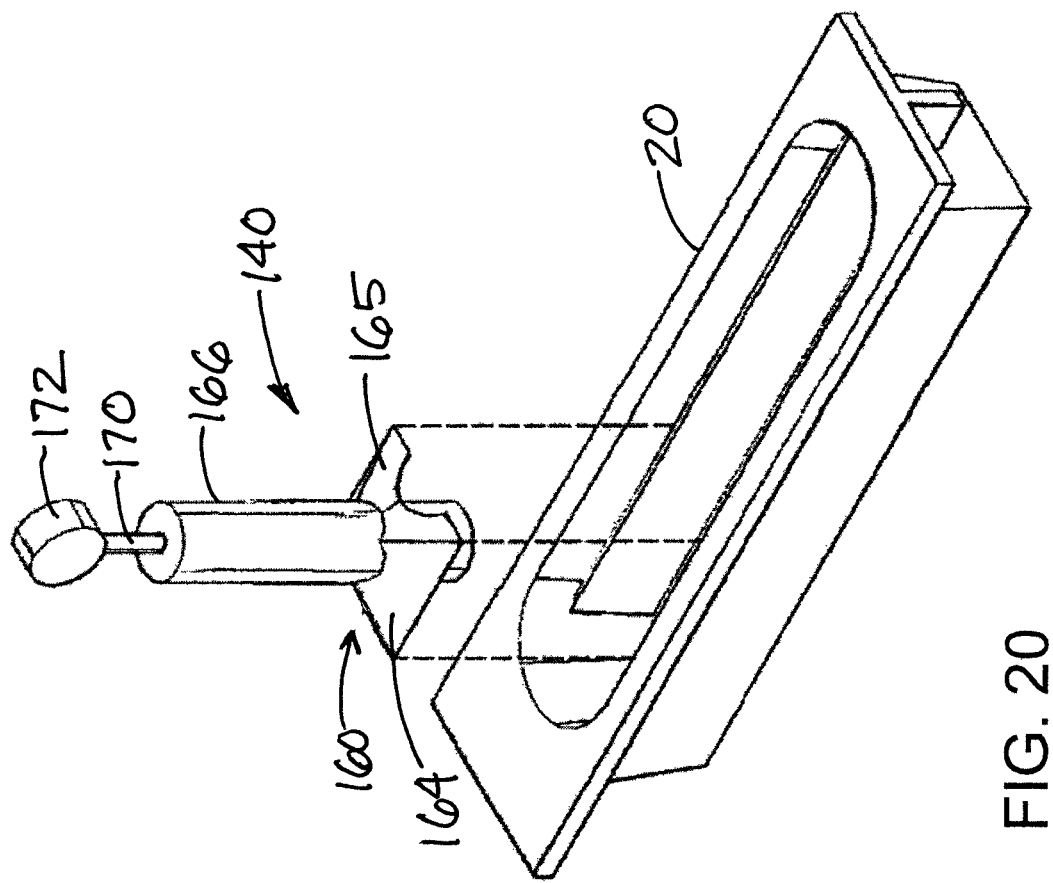
FIG. 20 is a schematic perspective view of another illustrative embodiment of a gas capture structure shown in exploded relationship with a trough.

In another illustrative embodiment of the gas capture structure shown in FIGS. 20 and 21, the gas capture tube may be mounted on a saddle 160 for attachment to the trough. The saddle 160 may have opposite mounting edges 162, 163 for engaging the side sections of the perimeter wall of the trough. The saddle 160 may have mounting flanges 164, 165 which extend in opposite directions from the gas capture tube. The mounting edges 162, 163 may be located on the mounting flanges 164, 165. A suction element 166 may be at least partially positioned in the gas capture chamber. The suction element 166 may include a piston 168 which is movably positioned in the gas capture chamber, a rod 170 which is connected to the piston 168 and extends through the upper end 146 of the gas capture tube, and the handle 172 which is located outside of the gas capture chamber and may be mounted on the rod 170 at locations opposite of the piston 168. The handle may be operated by the user to push the piston to move any gas out of the gas capture chamber to purge the chamber, and may also be used to draw the medium on the trough into the chamber.

Figure 22:
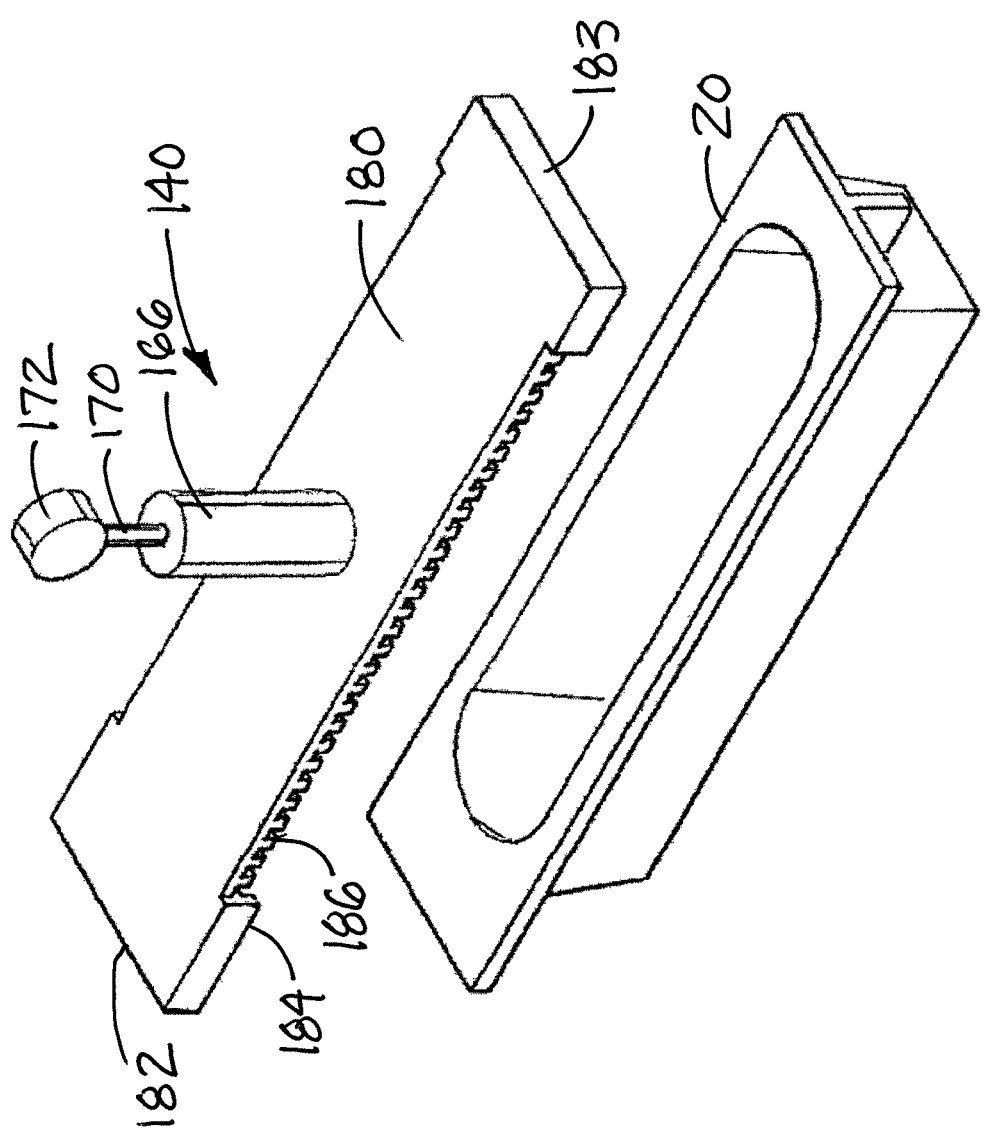
FIG. 22 is a schematic perspective view of still another illustrative embodiment of a gas capture structure shown in exploded relationship with a trough.
Figure 23:
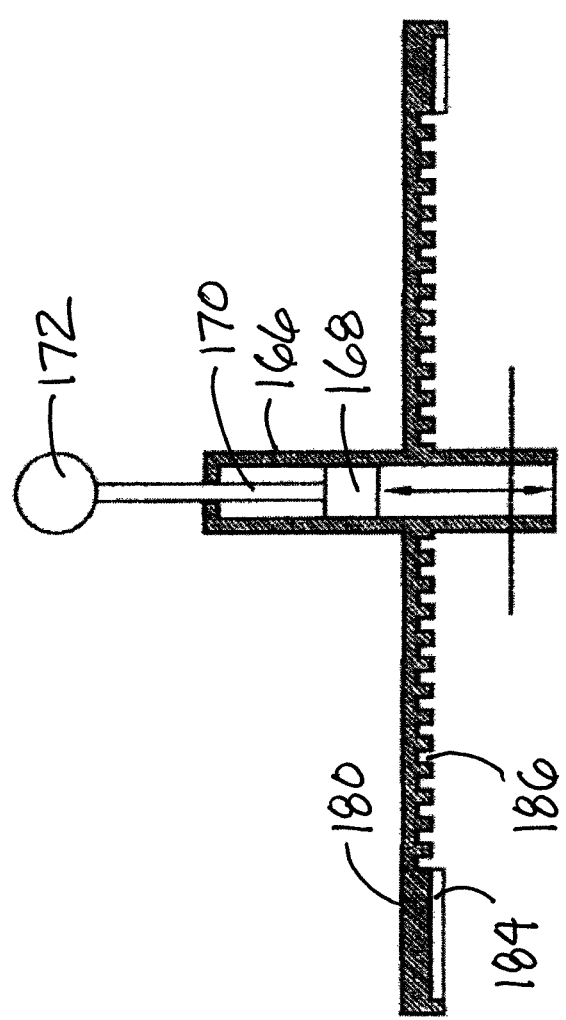
FIG. 23 is a schematic side sectional view of the gas capture structure shown in FIG. 22.

In yet another illustrative embodiment of the gas capture structure shown in FIGS. 22 and 23, the gas capture tube may be mounted on a cap 180 for attachment to the trough 20. The gas capture tube may extend through the cap. The cap 180 may have opposite mounting ends 182, 183 for engaging the ends of the trough. The cap 180 may have a lower surface 184 which may have a plurality of grooves 186 formed thereon. The grooves 186 may extend substantially parallel to each other and may extend laterally with respect to the length of the cap. The gas capture tube may also include the suction element which may be utilized in substantially the same manner.

It should be appreciated that in the foregoing description and appended claims, that the terms "substantially" and "approximately," when used to modify another term, mean "for the most part" or "being largely but not wholly or completely that which is specified" by the modified term.

It should also be appreciated from the foregoing description that, except when mutually exclusive, the features of the various embodiments described herein may be combined with features of other embodiments as desired while remaining within the intended scope of the disclosure.

Further, those skilled in the art will appreciate that steps set forth in the description and/or shown in the drawing figures may be altered in a variety of ways. For example, the order of the steps may be rearranged, substeps may be performed in parallel, shown steps may be omitted, or other steps may be included, etc.

With respect to the above description then, it is to be realized that the optimum dimensional relationships for the parts of the disclosed embodiments and implementations, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosed subject matter to the exact construction and operation shown and described, and accordingly, all suitable modifications and equivalents may be resorted to that fall within the scope of the claims.

I claim:

1. A system comprising:
 a base assembly having a top and a bottom restable on a surface, the base assembly comprising:
  a trough holder defining a plurality of bays; and
  a plurality of troughs each removably mounted in one of the bays of the plurality of bays of the trough holder, each of the troughs having an upper opening into a cavity of the trough, each of the troughs being elongated between opposite ends such that the upper opening in the cavity of the trough is elongated between the opposite ends of the trough, each of the troughs having:
   a base wall;
   a perimeter wall extending upwardly from the base wall to define the cavity of the trough; and
   an upper lip wall defining the upper opening of the trough, the upper lip wall extending outwardly from the perimeter wall outwardly to a perimeter edge of the trough, the perimeter edge being positioned adjacent to the perimeter edge of another trough positioned in an adjacent bay of the plurality of bays of the trough holder;
 a cover assembly removably mounted on the base assembly to cover the plurality of bays of the trough holder and the plurality of troughs mounted on the trough holder, the cover assembly comprising:
  a main cover portion including:
   a cover wall extending over the troughs mounted on the trough holder, the cover wall having an upper surface and a lower surface, the cover wall having a periphery with opposite sides; and
   a peripheral wall extending along the periphery of the cover wall and extending downwardly about a portion of the trough holder;
   wherein the cover wall includes an aperture for each one of the bays of the plurality of bays of the trough holder of the base assembly, the aperture for an associated bay of the plurality of bays extending through the cover wall and being vertically aligned with the associated bay such that the aperture is vertically aligned with the cavity of said trough mounted on the base assembly in the associated bay;
   wherein the aperture includes a tubular structure immovably united to the cover wall such that the tubular structure is carried by and removed with the main cover portion from the base assembly, the tubular structure of said aperture having a lower portion extending downwardly from the cover wall toward the cavity of the trough mounted in the associated bay of the trough holder, the lower portion having a lowermost end opposite of the cover wall on the lower portion, the peripheral wall of the main cover portion extending further from the cover wall than the lowermost end of the tubular structure, the tubular structure of said aperture defining a channel to guide movement of a disk moving through the aperture toward the cavity, the tubular structure of the aperture having an upper portion extending upwardly from the cover wall above a plane of the upper surface of the cover wall to guide movement of a disk into the channel and through the cover wall to the lowermost end of the tubular structure; and
   wherein a perimeter shoulder is formed on the trough holder along a perimeter of the base assembly, the peripheral wall of the main cover portion of the cover assembly resting upon the perimeter shoulder when the cover assembly is mounted on the base assembly to position the tubular structures of the apertures of the cover assembly with respect to the plurality of troughs of the base assembly;
  a disc pressure portion pivotally mounted on the main cover portion, the disc pressure portion including:
   a support wall; and
   a plurality of pressure posts mounted on the support wall at positions on the support wall such that pivot movement of the disc pressure portion with respect to the main cover portion to align each pressure post with the channel of the tubular structure of said aperture on the cover wall of the main cover portion;

wherein the disc pressure portion is pivotable with respect to the main cover portion between a raised position in which the disc pressure portion is moved away from the main cover portion and a lowered position in which the disc pressure portion is moved adjacent to the cover wall of the main cover portion, the disc pressure portion being pivotally movable in a first pivot direction to align and insert the pressure post of the disc pressure portion into the aperture to contact and press against a disc when the disc has been previously positioned in the channel and thereby move the disc toward the cavity of the trough, the disc pressure portion being pivotally movable in a second pivot direction to withdraw the pressure post from the aperture.

2. The system of claim 1 wherein each pressure post is elongated downwardly from the support wall and has a uniform width from a base of the pressure post to a tip of the pressure post.

3. The system of claim 1 wherein the disc pressure portion covers approximately one half of the main cover portion in the lowered position.

4. The system of claim 1 wherein each pressure post moves along an arcuate path in the first pivot direction and in the second pivot direction.

5. The system of claim 1 additionally comprising an agar material positioned in the cavity of at least one-trough of the plurality of troughs.

6. The system of claim 5 additionally comprising a covering strip removably mounted on the at least one trough to cover the upper opening of the at least one trough.

7. The system of claim 1 wherein a section of the tubular structure above the plane of the upper surface is removed to facilitate sliding of a disc across the upper surface of the cover wall and into the channel of the tubular structure of the aperture.

8. The system of claim 7 wherein the main cover portion includes an arcuate ridge located on the upper surface of the cover wall, the arcuate ridge extending between remaining sections of the tubular structures of adjacent apertures to form a serpentine shape with the remaining sections of the tubular structures associated with the plurality of the apertures for guiding movement of a disk slid across the upper surface of the cover wall to one of the apertures.

9. The system of claim 1 wherein at least one trough of the plurality of troughs has:
   a needle hole extending through the perimeter wall of the at least one trough below the upper opening; and
   an insertion needle configured to be inserted into the cavity of the at least one trough through the needle hole.

10. The system of claim 1 additionally comprising a securing structure configured to removably secure at least one trough of the plurality of troughs in a bay of the plurality of bays.

11. The system of claim 10 wherein the securing structure includes a first securing structure comprising:
   a blade located on a first end of the at least one trough and a slot located on a corresponding first end of the bay of the plurality of bays; and
   a second securing structure comprising a plug located on a second end of the at least one trough and a recess located on a corresponding second end of the bay of the plurality of bays.

12. The system of claim 1 wherein the troughs of the plurality of troughs are transparent; and additionally comprising:
   a measuring surface having an upper measuring surface on which the trough holder with the plurality of troughs of the base assembly is rested, the measuring surface having a plurality of gradated markings, the gradated markings each comprising a straight line extending across a portion of the measuring surface, the lines of the markings being oriented substantially parallel to each other such that, when the plurality of troughs in the trough holder are positioned on the upper measuring surface, inhibition zones in media in the plurality of troughs are comparable by viewing the lines through the plurality of troughs and the media.

13. A system comprising:
   a base assembly having a top and a bottom restable on a surface, the base assembly comprising a trough holder defining a plurality of bays;
   at least one trough having an upper opening into a cavity configured to receive a quantity of a medium, the at least one trough being removably mountable in one of the bays of the plurality of bays of the trough holder;
   a cover assembly removably mounted on the base assembly to cover the upper opening of the at least one trough in the holder, the cover assembly comprising:
      a main cover portion including a cover wall extending over the at least one trough, at least one aperture extending through the main cover portion and being vertically aligned with the cavity of the at least one trough mounted on the base assembly; and
      a disc pressure portion movably mounted on the main cover portion, the disc pressure portion being movable with respect to the main cover portion to insert an element of the disc pressure portion into the at least one aperture to press against a disc positioned at the aperture of the main cover portion to move the disc toward the cavity of the at least one trough and into contact with medium in the cavity; and
   a gas capture structure removably mountable on the at least one trough to cover at least a portion of the upper opening of the at least one trough, the gas capture structure defining a gas capture chamber with the cavity of the at least one trough, the gas capture structure being configured to capture gases in the gas capture chamber generated after pressing of the disc into contact with the medium by the disc pressure portion, the gas capture structure and the at least one trough being separable as a unit from the trough holder;
   wherein the gas capture structure includes a gas capture tube that defines the gas capture chamber.

* * * * *